US006379946B1

(12) United States Patent
Ensign et al.

(10) Patent No.: US 6,379,946 B1
(45) Date of Patent: Apr. 30, 2002

(54) INSECTICIDAL PROTEIN TOXINS FROM XENORHABDUS

(75) Inventors: Jerald C. Ensign, Madison; David J. Bowen, Oregon; Jennifer L. Tenor, Madison, all of WI (US); James K. Petell, Zionsville, IN (US); Gregory L. Orr, Indianapolis, IN (US); Scott B. Bintrim, Carmel, IN (US); Todd A. Ciche, Madison, WI (US); James A. Strickland, Lebanon; Raymond O. Fatig, Zionsville, both of IN (US); Richard H. Ffrench-Constant, Madison, WI (US)

(73) Assignee: Wisconsin Alumn Research Foundation, Madison, WI (US)

( * ) Notice: Subject to any disclaimer, the term of this patent is extended or adjusted under 35 U.S.C. 154(b) by 0 days.

(21) Appl. No.: 09/514,739

(22) Filed: Feb. 28, 2000

Related U.S. Application Data

(62) Division of application No. 09/072,264, filed on May 4, 1998, now Pat. No. 6,048,838.
(60) Provisional application No. 60/045,641, filed on May 5, 1997.

(51) Int. Cl.$^7$ .......................... C12N 1/20; A01N 63/00
(52) U.S. Cl. .................... 435/252.1; 435/822; 424/93.4
(58) Field of Search ............................ 514/2; 530/350; 435/252.1, 822; 424/93.4

(56) References Cited

U.S. PATENT DOCUMENTS 5,616,318 A   4/1997   Dudney ..................... 424/93.1

FOREIGN PATENT DOCUMENTS

| WO | WO 95/00647 | 1/1995 |
| WO | WO 97/17432 | 5/1997 |
| WO | WO 98/08388 | 3/1998 |

OTHER PUBLICATIONS

David Joseph Bowen, "Characterization of a High Molecular Weight Insecticidal Protein Complex Produced by the Entomopathogenic Bacterium *Photorhabdus luminescens*" Ph.D. Thesis May 1995 U. Wisc.

Hongsthong, A. et al. "Optimum conditions for insecticidal toxin production by *Photorhabdus luminescens*." Abstracts of the General Meeting of the AmericanSociety for Microbiology, vol. 95, May 1995, pp. 408.

Akhurst et al, "A numerical taxonomic study of the genus Xenorhabdus (Enterobacteriaceae) and proposed elevatio of the subspecies of *X. nematophilus* to species." Journal of General Microbiology, vol. 134, No.7, Jul. 1988, pp. 1835–1845.

J. Jarosz et al. "Involvement of larvicidal toxins in pathogenesis of insect parasitism with the rhabditoid nematodes, *Steinernema feltiae* and *Heterorhabditis bacteriophora*." Entomophaga, vol. 36, No. 3, 1991. pp. 361–368.

M. Balcerzak, "Comparative studies on parasitism caused by entomogenous nematodes, *Stenernema feltiae* and *Heterorhabditis bacteriophora*." Acta Parasitologica Polonica, 1991, vol. 36, No. 4, pp. 175–181.

S. Frost et al. "Molecular Biology of the Symbiotic–Pathogenic Bacteria Xenorhabdus spp. and Photrhabdus spp." Microbiological Reviews, Mar. 1996, vol. 60, pp. 21–43.

S. Frost et al. "Xenorhabdus and Photorhabdus spp.: Bugs that kill bugs," Annu. Rev. Microbiol. 1997, vol. 51, pp. 47–72.

Bowen et al. Extracellular insecticidal factor produced by *Xenorhabdus luminescens*. Abstr. Ann.. Meeting Am. Soc. Microbiol.89$^{th}$ Meeting 228 (1989).

Burman. *Neoaplectana carpocapse:* Toxin produuction by axenic insect parasitic nematodes. Nematologica 28:62–70 (1982).

Creighton, T.E. Proteins: Structures and Molecular Properties, W.H. Freeman and Company, New York, pp. 23–27 (1993).

*Primary Examiner*—Gabrielle Bugaisky
(74) *Attorney, Agent, or Firm*—Donald R. Stuart (57) ABSTRACT

Proteins from the genus Xenorhabdus are toxic to insects upon oral exposure. These protein toxins can be applied to insect larvae food and plants for insect control.

1 Claim, 1 Drawing Sheet

FIG. 1

INSECTICIDAL PROTEIN TOXINS FROM XENORHABDUS

CROSS-REFERENCE TO RELATED APPLICATIONS

This patent application is a divisional application of U.S. Ser. No. 09/072,264, filed May 4, 1998, U.S. Pat. No. 6,048,838 which claimed priority from a U.S. Provisional patent application Ser. No. 60/045,641 filed on May 5, 1997.

This invention was made with United States government support awarded by the following agencies:

USDA Hatch Grant No: 5206.

The United States has certain rights in this invention.

FIELD OF THE INVENTION

The present invention relates to toxins isolated from bacteria and the use of said toxins as insecticides.

BACKGROUND OF THE INVENTION

In the past there has been interest in using biological agents as an option for pest management. One such method explored was the potential of insect control using certain genera of nematodes. Nematodes, like those of the Steinernema and Heterorhabditis genera, can be used as biological agents due in part to their transmissible insecticidal bacterial symbionts of the genera Xenorhabdus and Photorhabdus, respectively. Upon entry into the insect, the nematodes release their bacterial symbionts into the insect hemolymph where the bacteria reproduce and eventually cause insect death. The nematode then develops and reproduces within the cadaver. Bacteria-containing nematode progeny exit the insect cadaver as infective juveniles which can then invade additional larvae thus repeating the cycle leading to nematode propagation. While this cycle is easily performed on a micro scale in a laboratory setting, adaptation to the macro level, as needed to be effective as a general use insecticide, is difficult, expensive, and inefficient to produce, maintain, distribute and apply.

In addition to biological approaches to pest management such as nematodes, there are now pesticide control agents commercially available that are naturally derived. These naturally derived approaches can be as effective as synthetic chemical approaches. One such naturally occurring agent is the crystal protein toxin produced by the bacteria *Bacillus thuringiensis* (Bt). These protein toxins have been formulated as sprayable insect control agents. A more recent application of Bt technology has been to isolate and transform into plants the genes that produce the toxins. Transgenic plants subsequently produce the Bt toxins thereby providing insect control, (see U.S. Pat. Nos. 5,380,831; 5,567,600; and 5,567,862 to Mycogen in San Diego, Calif.).

Transgenic Bt plants are quite efficacious and usage is predicted to be high in some crops and areas. This has caused a concern that resistance management issues may arise more quickly than with traditional sprayable applications. Thus, it would be quite desirable to discover other bacterial sources distinct from Bt which produce toxins that could be used in transgenic plant strategies, or could be combined with Bts to produce insect controlling transgenic plants.

It has been known in the art that bacteria of the genus Xenorhabdus are symbiotically associated with the Steinernema nematode. Unfortunately, as reported in a number of articles, the bacteria only had pesticidal activity when injected into insect larvae and did not exhibit biological activity when delivered orally (see Jarosz J. et al. "Involvement of Larvicidal Toxins in Pathogenesis of Insect Parasitism with the Rhabditoid Nematodes, *Steinernema Feltiae* and *Heterorhabditis Bacteriophora*" Entomophaga 36 (3) 1991 361–368; Balcerzak, Malgorzata "Comparative studies on parasitism caused by entomogenous nematodes, *Steinernema feltiae* and *Heterorhabditis bacteriophors* I. The roles of the nematode-bacterial complex, and of the associated bacteria alone, in pathogenesis" Acta Parasitologica Polonica, 1991, 36(4); 175–181).

For the reasons stated above it has been difficult to effectively exploit the insecticidal properties of the nematode orits bacterial symbiont. Thus, it would be quite desirable to discover proteinaceous agents derived from Xenorhabdus bacteria that have oral activity so that the products produced therefrom could either be formulated as a sprayable insecticide or the bacterial genes encoding said proteinaceous agents could be isolated and used in the production of transgenic plants. Until applicants' invention herein there was no known Xenorhabdus species or strains that produced protein toxin(s) having oral activity.

SUMMARY OF THE INVENTION

The native toxins are protein complexes that are produced and secreted by growing bacterial cells of the genus Xenorhabdus. The protein complexes, with a native molecular size ranging from about 800 to 3000 kDa, can be separated by SDS-PAGE gel analysis into numerous component proteins. The toxins exhibit significant toxicity upon exposure to a number of insects. Furthermore, toxin activity can be modified by altering media conditions. In addition, the toxins have characteristics of being proteinaceous in that the activity thereof is heat labile and sensitive to proteolysis.

The present invention provides an easily administered functional protein.

The present invention also provides a method for delivering insecticidal toxins that are functionally active and effective against many orders of insects.

Objects, advantages, and features of the present invention will become apparent from the following specification.

BRIEF DESCRIPTION OF THE DRAWINGS

FIG. 1 is a phenogram of Xenorhabdus strains as defined by rep-PCR. The upper axis of FIG. 1 measures the percentage similarity of strains based on scoring of rep-PCR products (i.e., 0.0 [no similarity] to 1.0 [100% similarity]). At the right axis, the numbers and letters indicate the various strains tested. Vertical lines separating horizontal lines indicate the degree of relatedness (as read from the extrapolated intersection of the vertical line with the upper axis) between strains or groups of strains at the base of the horizontal lines (e.g., strain DEX1 is about 83% similar to strain X. nem).

DETAILED DESCRIPTION OF THE INVENTION

The present inventions are directed to discovery of a unique class of functional protein toxins as defined herein produced by bacteria of the genus Xenorhabdus, said toxins having oral toxicity against insects. Xenorhabdus species/strains may be isolated from a variety of sources. One such source is entomopathogenic nematodes, more particularly nematodes of the genus Steinernema or from insect cadavers infested by these nematodes. It is possible that other sources could harbor Xenorhabdus bacteria that produce insecticidal toxins having functional activity. Such sources in the environment could be either terrestrial or aquatic based.

The genus Xenorhabdus is taxonomically defined as a member of the Family Enterobacteriaceae, although it has certain traits atypical of this family. For example, strains of this genus are typically nitrate reduction negative, and catalase negative. Xenorhabdus has only recently been subdivided to create a second genus; Photorhabdus which is comprised of the single species Photorhabdus luminescens (previously Xenorhabdus luminescens) (Boemare et al., 1993 Int. J. Syst. Bacteriol. 43, 249–255). This differentiation is based on several distinguishing characteristics easily identifiable by the skilled artisan. These differences include the following: DNA-DNA characterization studies; phenotypic presence (Photorhabdus) or absence (Xenorhabdus) of catalase activity; presence (Photorhabdus) or absence (Xenorhabdus) of bioluminescence; the Family of the nematode host in that Xenorhabdus is found in Steinernematidae and Photorhabdus is found in Heterorhabditidae); as well as comparative, cellular fatty-acid analyses (Janse et al. 1990, Lett. Appl. Microbiol 10, 131–135; Suzuki et al. 1990, J. Gen. Appl. Microbiol., 36, 393–401). In addition, recent molecular studies focused on sequence (Rainey et al. 1995, Int. J. Syst. Bacteriol., 45, 379–381) and restriction analysis (Brunel et al., 1997, App. Environ. Micro., 63, 574–580) of 16S rRNA genes also support the separation of these two genera. This change in nomenclature is reflected in this specification, but in no way should a future change in nomenclature alter the scope of the inventions described herein.

In order to establish that the strains disclosed herein were comprised of Xenorhabdus strains, the strains were characterized based on recognized traits which define Xenorhabdus species/strains and differentiate them from other Enterobacteriaceae and Photorhabdus species/strains. (Farmer, 1984 Bergey's Manual of Systemic Bacteriology Vol. 1, pp. 510–511; Akhurst and Boemare 1988, J. Gen. Microbiol. 134, pp. 1835–1845; Boemare et al. 1993 Int. J. Syst. Bacteriol. 43, pp. 249–255, which are incorporated herein by reference). The expected traits for Xenorhabdus are the following: Gram stain negative rods, organism size of 0.3–2×2–10 µm, white to yellow/brown colony pigmentation, presence of inclusion bodies, absence of catalase, inability to reduce nitrate, absence of bioluminescence, ability to uptake dye from medium, positive gelatin hydrolysis, growth on Enterobacteriaceae selective media, growth temperature below 37° C., survival under anaerobic conditions, and motility.

Currently, the bacterial genus Xenorhabdus is comprised of four recognized species, Xenorhabdus nematophilus, Xenorhabdus poinarii, Xenorhabdus bovienii and Xenorhabdus beddingii (Brunel et al., 1997, App. Environ. Micro., 63, 574–580). A variety of related strains have been described in the literature (e.g., Akhurst and Boemare 1988 J. Gen. Microbiol., 134, 1835–1845; Boemare et al. 1993 Int. J. Syst. Bacteriol. 43, pp. 249–255; Putz et al. 1990, Appl. Environ. Microbiol., 56, 181–186, Brunel et al., 1997, App. Environ. Micro., 63, 574–580, Rainey et al. 1995, Int. J. Syst. Bacteriol., 45, 379–381). Numerous Xenorhabdus strains have been characterized herein. Such strains and the characteristics thereof are listed in Table 3 in the Examples. These strains have been deposited with the Agricultural Research Service Patent Culture Collection (NRRL) at 1815 North University Street Peoria, Ill. 61604 U.S.A. The deposited strains and the corresponding deposit dates and deposit numbers are indicated in the following table:

| Strain | Date of Deposit | Deposit Number |
| --- | --- | --- |
| S. carp | Apr. 29, 1997 | NRRL-B-21732, |
| X. Wi | Apr. 29, 1997 | NRRL-B-21733, |
| X. nem | Apr. 29, 1997 | NRRL-B-21734, |
| X. NH3 | Apr. 29, 1997 | NRRL-B-21735, |
| X. riobravis | Apr. 29, 1997 | NRRL-B-21736 |
| GL133B | Apr. 29, 1997 | NRRL-B-21737, |
| DEX1 | Apr. 29, 1997 | NRRL-B-21738, |
| DEX2 | Apr. 29, 1997 | NRRL-B-21739, |
| DEX3 | Apr. 29, 1997 | NRRL-B-21740, |
| DEX4 | Apr. 29, 1997 | NRRL-B-21741, |
| DEX5 | Apr. 29, 1997 | NRRL-B-21742, |
| DEX6 | Apr. 29, 1997 | NRRL-B-21743, |
| DEX7 | Apr. 30, 1998 | NRRL-B-30008, |
| DEX8 | Apr. 30, 1998 | NRRL-B-30028, |
| ILM037 | Apr. 30, 1998 | NRRL-B-30009, |
| ILM039 | Apr. 30, 1998 | NRRL-B-30010, |
| ILM070 | Apr. 30, 1998 | NRRL-B-30011, |
| ILM078 | Apr. 30, 1998 | NRRL-B-30012, |
| ILM079 | Apr. 30, 1998 | NRRL-B-30013, |
| ILM080 | Apr. 30, 1998 | NRRL-B-30014, |
| ILM081 | Apr. 30, 1998 | NRRL-B-30015, |
| ILM082 | Apr. 30, 1998 | NRRL-B-30016, |
| ILM083 | Apr. 30, 1998 | NRRL-B-30017, |
| ILM084 | Apr. 30, 1998 | NRRL-B-30018, |
| ILM102 | Apr. 30, 1998 | NRRL-B-30019, |
| ILM103 | Apr. 30, 1998 | NRRL-B-30020, |
| ILM104 | Apr. 30, 1998 | NRRL-B-30021, |
| ILM129 | Apr. 30, 1998 | NRRL-B-30022, |
| ILM133 | Apr. 30, 1998 | NRRL-B-30023, |
| ILM135 | Apr. 30, 1998 | NRRL-B-30024, |
| ILM138 | Apr. 30, 1998 | NRRL-B-30025, |
| ILM142 | Apr. 30, 1998 | NRRL-B-30026, |
| ILM143 | Apr. 30, 1998 | NRRL-B-30027, |
| GLX26 | Apr. 30, 1998 | NRRL-B-30002, |
| GLX40 | Apr. 30, 1998 | NRRL-B-30003, |
| GLX166 | Apr. 30, 1998 | NRRL-B-30004, |
| SEX20 | Apr. 30, 1998 | NRRL-B-30005, |
| SEX76 | Apr. 30, 1998 | NRRL-B-30006, |
| SEX180 | Apr. 30, 1998 | NRRL-B-30007. |

Figure 1:
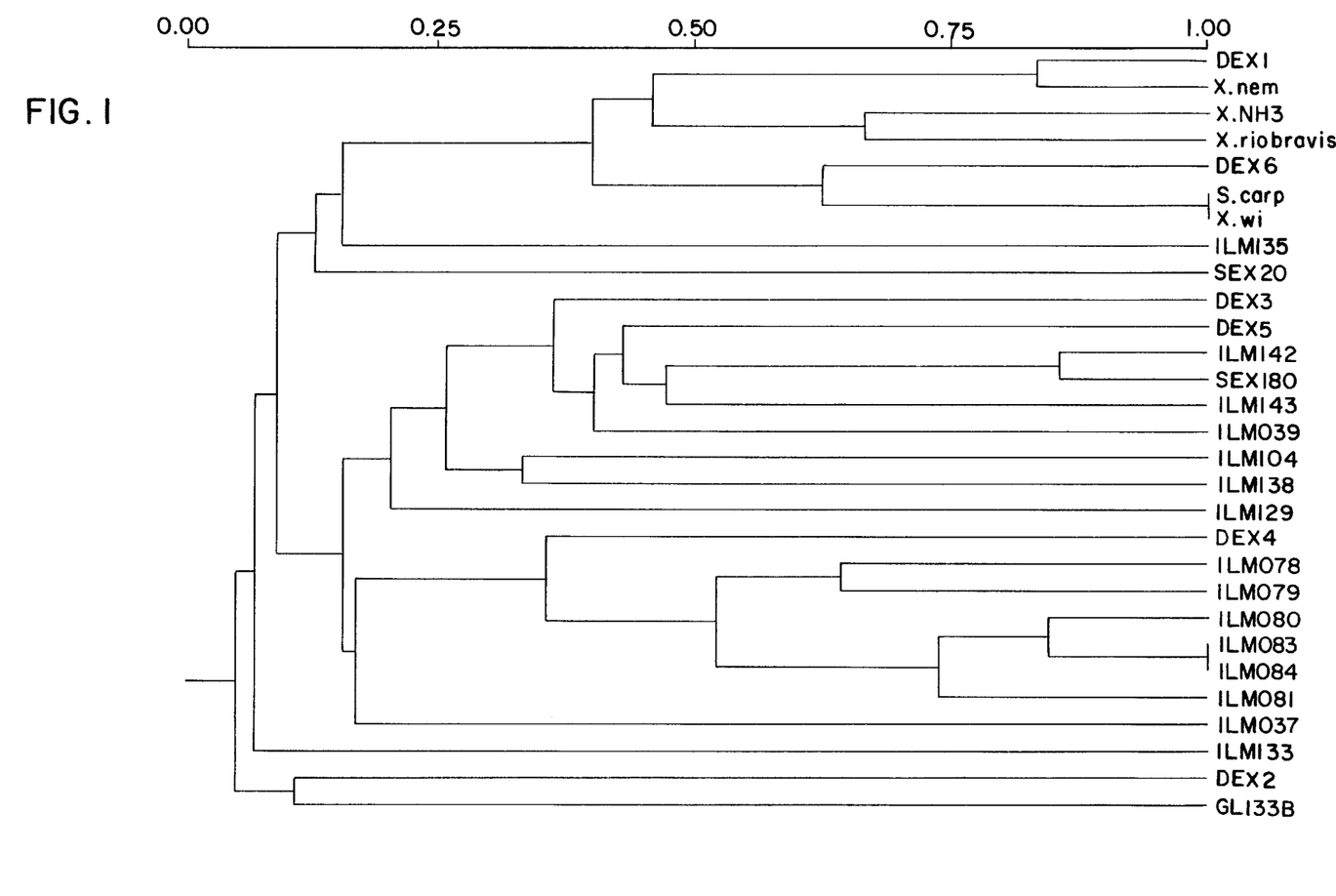

As can be seen in FIG. 1, these strains are diverse. It is not unforeseen that in the future there may be other Xenorhabdus species that will have some or all of the attributes of the described species as well as some different characteristics that are presently not defined as a trait(s) of Xenorhabdus. However, the scope of the invention herein is to any Xenorhabdus species or strains which produce proteins as described herein that have functional activity as orally active insect control agents, regardless of other traits and characteristics. Further included within the inventions are the strains specified herein and any mutants or phase variants thereof.

There are several terms that are used herein that have a particular meaning and are as follows:

By "functional activity" it is meant herein that the protein toxins function as orally active insect control agents, that the proteins have a toxic effect, or are able to disrupt or deter insect feeding which may or may not cause death of the insect. When an insect comes into contact with an effective amount of toxin derived from Xenorhabdus delivered via transgenic plant expression, formulated protein compositions(s), sprayable protein composition(s), a bait matrix or other delivery system, the results are typically death of the insect, or the insects do not feed upon the source which makes the toxins available to the insects.

By "native size" is meant the undenatured size of the protein toxin or protein toxin subunit produced by the Xenorhabdus strain of interest prior to any treatment or modification. Native sizes of proteins can be determined by a variety of methods available to the skilled artisan including but not limited to gel filtration chromatography, agarose and polyacrylamide gel electrophoresis, mass spectroscopy, sedimentation coefficients and the like. Treatment or modifications to alter protein native size can be performed by proteolysis, mutagenesis, gene truncation, protein unfolding and other such techniques available to the artisan skilled in the art of protein biochemistry and molecular biology.

The protein toxins discussed herein are typically referred to as "insecticides". By insecticides it is meant herein that the protein toxins have a "functional activity" as further defined herein and are used as insect control agents.

The term "toxic" or "toxicity" as used herein is meant to convey that the toxins produced by Xenorhabdus have "functional activity" as defined herein.

The term "Xenorhabdus toxin" is meant to include any protein produced by a Xenorhabdus microorganism strain having functional activity against insects, where the Xenorhabdus toxin could be formulated as a sprayable composition, expressed by a transgenic plant, formulated as a bait matrix, delivered via a baculovirus, a plant RNA viral based system, or delivered by any other applicable host or delivery system. It is also meant to include any sequence of amino acids, polypeptides peptide fragment or other protein preparation, whether derived in whole or in part from natural or synthetic sources which demonstrates the ability to exhibit functional activity as disclosed herein. Typically, a Xenorhabdus toxin will be derived in whole or in part from a Xenorhabdus bacterial source.

The term "Xenorhabdus toxin" is also meant to include modified amino acid sequences, such as sequences which have been mutated, truncated, increased and the like, as well as such sequences which are partially or wholly artificially synthesized. Xenorhabdus toxins and nucleic acid sequences encoding said toxins may be obtained by partial or homogenous purification of bacterial extracts, N-terminal or internal amino acid sequence information, protein modeling, nucleic acid probes, antibody preparations, or sequence comparison. Once a purified or partially purified Xenorhabdus toxin is obtained, it may be used to obtain other Xenorhabdus toxins by immunoprecipitation involving the formation of an antigen:antibody immunocomplex thereby allowing recovery of the new toxin which reacts thereto. Once the nucleic acid sequence encoding a Xenorhabdus toxin is obtained, it may be employed in probes for further screening or used in genetic engineering constructs for transcription or transcription and translation in host cells.

Fermentation broths from selected strains reported in Table 3 were used to examine the following: breadth of insecticidal toxins having functional activity produced by the Xenorhabdus genus, the functional spectrum of these toxins, and the protein components of said toxins. The strains characterized herein have been shown to have oral toxicity against a variety of insect orders. Such insect orders include but are not limited to Coleoptera, Lepidoptera, Diptera, and Acarina.

As with other bacterial toxins, the mutation rate of bacteria in a population may result in the variation of the sequence of toxin genes. Toxins of interest here are those which produce proteins having functional activity against a variety of insects upon exposure, as described herein. Preferably, the toxins are active against Lepidoptera, Coleoptera, Diptera, and Acarina. The inventions herein are intended to capture the protein toxins homologous to protein toxins produced by the strains herein and any derivative strains thereof, as well as any other protein toxins produced by Xenorhabdus that have functional activity. These homologous proteins may differ in sequence, but do not differ in functional activity from those toxins described herein. Homologous toxins are meant to include protein complexes of between 100 kDa to 3500 kDa and are comprised of at least one subunit, where a subunit is a peptide which may or may not be the same as the other subunit.

The toxins described herein are quite unique in that the toxins have functional activity, which is key to developing an insect management strategy. In developing an insect management strategy, it is possible to delay or circumvent the protein degradation process by injecting a protein directly into an organism, avoiding its digestive tract. In such cases, the protein administered to the organism will retain its function until it is denatured, non-specifically degraded, or eliminated by the immune system in higher organisms. Injection into insects of an functional toxin has potential application only in the laboratory.

The discovery that the functional protein toxins herein exhibit their activity after oral ingestion or contact with the toxins permits the development of an insect management plan based solely on the ability to incorporate the protein toxins into the insect diet. Such a plan could result in the production of insect baits.

The Xenorhabdus toxins may be administered to insects in both a purified and non-purified form. The toxins may also be delivered in amounts from about 1 to about 1000 mg/liter of broth. This may vary upon formulation condition, conditions of the inoculum source, techniques for isolation of the toxin, and the like. The toxins found herein can be administered as a sprayable insecticide. Fermentation broth from Xenorhabdus can be produce, diluted, or if needed, be concentrated about 100 to 1000-fold using ultrafiltration or other techniques available to the skilled artisan. Treatments can be applied with a syringe sprayer, a track sprayer or any such equipment available to the skilled artisan wherein the broth is applied to the plants. After treatments, broths can be tested by applying the insect of choice to said sprayed plant and can the be scored for damage to the leaves. If necessary, adjuvants and photo-protectants can be added to increase toxin-environmental half-life. In a laboratory setting, broth, dilutions, or concentrates thereof can be applied using methods available to the skilled artisan. Afterwards, the material can be allowed to dry and insects to be tested are applied directly to the appropriate plant tissue. After one week, plants can be scored for damage using a modified Guthrie Scale (Koziel, M. G., Beland, G. L., Bowman, C., Carozzi, N. B., Crenshaw, R., Crossland, L., Dawson, J., Desai, N., Hill, M., Kadwell, S., Launis, K., Lewis, K., Maddox, D., McPherson, K., Meghji, M. Z., Merlin, E., Rhodes, R., Warren, G. W., Wright, M. and Evola, S. V. 1993). In this manner, broth or other protein containing fractions may confer protection against specific insect pests when delivered in a sprayable formulation or when the gene or derivative thereof, encoding the protein or part thereof, is delivered via a transgenic plant or microbe.

The toxins may be administered as a secretion or cellular protein originally expressed in a heterologous prokaryotic or eukaryotic host. Bacteria are typically the hosts in which proteins are expressed. Eukaryotic hosts could include but are not limited to plants, insects and yeast. Alternatively, the toxins may be produced in bacteria or transgenic plants in the field or in the insect by a baculovirus vector. Typically, insects will be exposed to toxins by incorporating one or more of said toxins into the food/diet of the insect.

Complete lethality to feeding insects is preferred, but is not required to achieve functional activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects since the ultimate objective is protection of insect-induced plant damage rather than insect death.

There are many other ways in which toxins can be incorporated into an insect's diet. For example, it is possible to adulterate the larval food source with the toxic protein by spraying the food with a protein solution, as disclosed herein. Alternatively, the purified protein could be genetically engineered into an otherwise harmless bacterium, which could then be grown in culture, and either applied to the food source or allowed to reside in the soil in an area in which insect eradication was desirable. Also, the protein could be genetically engineered directly into an insect food source. For instance, the major food source for many insect larvae is plant material. Therefore the genes encoding Xenorhabdus toxins can be transferred to plant material so that said plant material expresses the toxin of interest.

Transfer of the functional activity to plant or bacterial systems requires nucleic acid sequences encoding the amino acid sequences for the Xenorhabdus toxins integrated into a protein expression vector appropriate to the host in which the vector will reside. One way to obtain a nucleic acid sequence encoding a protein with functional activity is to isolate the native genetic material from the bacterial species or Xenorhabdus species which produce the toxins, using information deduced from the toxin's amino acid sequence, large portions of which are disclosed herein.

There are also many different fermentation conditions that can affect the amount or types of toxins produced by Xenorhabdus. Several different factors can be varied by the skilled artisan to optimize toxin production for increased or altered toxin activity. Such factors include but are not limited to aeration of media, temperature, media constituents such as phosphate, carbon sources, minerals, vitamins, sugars, nitrogen sources, pH and the like. Additional factors also include harvest time and the phase variant of the bacteria used.

Once broth containing toxin has been produce, there are many purification technique and chromatographic media available to the person skilled in the art of protein biochemistry to allow purification of Xenorhabdus toxins. After each and every step, fractions can be assayed to find those particular fractions having the functional activity of interest as described herein. For example, protein toxins can be enriched in the broth by centrifugation, membrane separation, and the like to form a highly enriched, concentrated solution of toxin being predominantly comprised of proteins having a native size greater than or equal to 100 kDa. The proteins can then fractionated by ion exchange chromatography where upon they are separated based on overall ionic charge. Again, fractions obtained therefrom can be assayed against a variety of insects as described herein to find those fractions having the protein toxins of interest. Said proteins can then be separated based on native size using gel filtration-size exclusion chromatography and the like. Typically, said fractions having functional activity appear to elute from gel filtration columns in a manner suggesting that the native toxin complex is about 500 kDa to about 3,250 kDa, preferably about 750 kDa to about 3000 kDa, with those in the range of about 800 kDa to about 1100 kDa being most preferred. Fractions containing the toxins of interest can then be further purified by using quantitative ion exchange, quantitative gel filtration, hydrophobic chromatography, isoelectric focusing and the like to again isolate highly enriched and purified toxin fractions. The manner and order of protein purification as described herein is exemplary only, thus other techniques and approaches used by the skilled artisan to enrich and isolate Xenorhabdus toxins are within the scope of this invention.

When applied to SDS-PAGE analysis, fractions containing high levels of Xenorhabdus toxin activity are shown to contain various protein subunits as taught in the Examples herein. Typically, the protein subunits are between about 20 kDa to about 350 kDa; between about 130 kDa to about 300 kDa; between about 200 kDa to about 220 kDa; about 40 kDa to about 80 kDa; and about 20 kDa to about 40 kDa.

Given the few bands provided in the SDS-PAGE, immediate efforts to obtain the corresponding amino acid and/or nucleic acid sequences thereto are possible in accordance with methods familiar to those skilled in the art. From such sequences, Xenorhabdus toxins may be further confirmed with expression in controlled systems, such as *E. coli* and the like. In addition, said sequences allow the production of antibodies recognizing said toxins which can then be used to identify related Xenorhabdus toxin in other bacterial systems using methods available to the skilled artisan.

Amino acid sequences of fragments corresponding to partially or fully purified protein preparations may be obtainable through digestion with a protease, such as trypsin, and sequencing of resulting peptide fragments. Amino acid are disclosed herein. Said sequences can be used to design oligonucleotides using the genetic code through reverse translation. DNA sequences can then be chosen for use in Polymerase Chain Reactions (PCR) using genomic DNA isolated from Xenorhabdus bacterial cells. The resulting PCR-generated sequences can then be used as labeled probes in screening genomic libraries. In this manner, the full length clones corresponding to the Xenorhabdus toxin proteins seen on the SDS-PAGE may be recovered if desired. Other Xenorhabdus toxin genes may be obtained by screening genomic libraries from other Xenorhabdus species and other bacteria in the family Enterobacteriaceae.

The complete genomic sequence of a Xenorhabdus toxin may be obtained by the screening of a genomic or cosmid library with a probe. Probes can be considerably shorter than the entire gene sequence, but should be at least about 10, preferably at least 15, more preferably at least 20 or so nucleotides in length. Longer oligonucleotides are also useful, up to the full length of the gene encoding the polypeptide of interest. Both DNA and RNA can be used as probes. In use, probes are typically labeled with $^{32}P$, biotinylated, and the like in a manner that allows for detection thereof. Said probes are often incubated with single stranded DNA from the source of which the gene is desired. Hybridization, or the act of the probe binding to the DNA, is detected usually after hybridization using nitrocellulose paper or nylon membranes by means of the label on said probe. Hybridization techniques are well known to the person skilled in the art of molecular biology. Thus Xenorhabdus toxin genes may be isolated.

Other Xenorhabdus toxin genes or nucleic acid sequences are obtainable from amino acid sequences provided herein. "Obtainable" refers to those Xenorhabdus toxins and genes thereof which have sufficiently similar sequences or "homology" to that of the native sequences of this invention to provide a orally active functional toxin. One skilled in the art will readily recognize that antibody preparations, nucleic acid probes (DNA and RNA) and the like may be prepared using the amino acid sequences disclosed herein and used to screen and recover other Xenorhabdus toxin nucleic acid sequences from other sources. Thus, sequences homologously related to or derivations of Xenorhabdus toxins disclosed herein are considered obtainable from the present invention.

"Homologously related" includes those nucleic acid and amino acid sequences which are identical or conservatively substituted as compared to the native sequence. Typically, a homologously related nucleic acid sequence will show at least about 60% homology, and more preferably at least about 70% homology to the probes created from using the amino acid sequences disclosed herein and those nucleic acid sequences obtained therefrom using those methods and techniques as disclosed herein. Homology is determined upon comparison of sequence information, e.g., nucleic acid or amino acid or through hybridization reactions. Homology is also intended to include conservative amino acid substitutions, which are will known in the art. Conservative amino acid substitutions include glutamic acid/aspartic acid; valine/isoleucine/leucine; serine/threonine; arginine/lysine; glutamine/asparagine; or any such substitution that results in no significant change in functional activity of said toxin when compared to the native toxin. Significant change as used herein is defined as at least a 50% change in activity based on molar amounts compared to said native toxin.

It is within the scope of the invention as disclosed herein that toxins may be truncated and still retain functional activity. By "truncated toxin" is meant that a portion of a toxin protein may be cleaved and yet still exhibit activity after cleavage. Cleavage can be achieved by proteases inside or outside of the insect gut. Furthermore, effectively cleaved proteins can be produced using molecular biology techniques wherein the DNA bases encoding said toxin are removed either through digestion with restriction endonucleases or other techniques available to the skilled artisan. After truncation, said proteins can be expressed in heterologous systems such as *E. coli,* baculoviruses, plant-based viral systems, yeast and the like and then placed in insect assays as disclosed herein to determine activity. Truncated toxins have been successfully produced with several insecticidal protein toxins in that several proteins have been shown in the art to retain functional activity while having less than the entire, full length protein present. Said truncated proteins having insecticidal activity include insect juvenile hormone esterase (U.S. Pat. No. 5,674,485 to the Regents of the University of California; and the insecticidal toxin isolated from the bacterium *Bacillus thuringiensis* (Adang et al., Gene 36:289–300 (1985) "Characterized full-length and truncated plasmid clones of the crystal protein of Bacillus thuringiensis subsp kurstaki HD-73 and their toxicity to Manduca sexta)". As used herein, the term "Xenorhabdus toxin" is also meant to include truncated versions thereof having functional activity.

Recombinant constructs containing a nucleic acid sequence encoding a Xenorhabdus toxin and heterologous nucleic acid sequences of interest may be prepared. By heterologous is meant any sequence which is not naturally found joined to the synthase sequence. Hence, by definition, a sequence joined to sequence not naturally found in a Xenorhabdus toxin is considered to be heterologous.

Constructs may be designed to produce Xenorhabdus toxins in either prokaryotic or eukaryotic cells. The expression of a Xenorhabdus toxin in a plant cell is of special interest. Moreover, the nucleic acid sequence encoding a Xenorhabdus toxin may be integrated into a plant host genome. By transcribing and translating a nucleic acid sequence encoding a Xenorhabdus toxin in a plant host, said plant is expected to exhibit properties whereby insects are discouraged from feeding. As stated herein, it is not necessary for an functional agent to exhibit insect mortality to be effective at controlling insects.

To obtain high expression of heterologous genes in plants it may be preferred to reengineer said genes so that they are more efficiently expressed in the cytoplasm of plant cells. Maize is one such plant where it may be preferred to reengineer the heterologous gene(s) prior to transformation to increase the expression level thereof in said plant. Therefore, an additional step in the design of genes encoding a Xenorhabdus toxin is the designed reengineering of a heterologous gene for optimal expression.

One reason for the reengineering a Xenorhabdus toxin for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a Xenorhabdus toxin for maize expression, more preferably referred to as plant optimized gene(s), is to generate a DNA sequence having a higher G+C content, and preferably one close to that of maize genes coding for metabolic enzymes. Another goal in the design of the plant optimized gene(s) encoding a Xenorhabdus toxin is to generate a DNA sequence in which the sequence modifications do not hinder translation.

The table below (Table 1) illustrates how high the G+C content is in maize. For the data in Table 1, coding regions of the genes were extracted from GenBank (Release 71) entries, and base compositions were calculated using the Macvector™ program (IBI, New Haven, Conn.). Intron sequences were ignored in the calculations.

Due to the plasticity afforded by the redundancy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within a mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In reengineering genes encoding a Xenorhabdus toxin for maize expression, the codon bias of the plant has been determined. The codon bias for maize is the statistical codon distribution that the plant uses for coding its proteins and the preferred codon usage is shown in Table 2. After determining the bias, the percent frequency of the codons in the gene(s) of interest is determined. The primary codons preferred by the plant should be determined as well as the second and third choice of preferred codons. Afterwards, the amino acid sequence of the Xenorhabdus toxin of interest is reverse translated so that the resulting nucleic acid sequence codes for exactly the same protein as the native gene wanting

TABLE 1

Compilation of G + C contents of protein coding regions of maize genes.

| Protein Class[a] | Range % G + C | Mean % G + C[b] |
|---|---|---|
| Metabolic Enzymes (76) | 44.4–75.3 | 59.0 ( ±8.0) |
| Structural Proteins (18) | 48.6–70.5 | 63.6 ( ±6.7) |
| Regulatory Proteins (5) | 57.2–68.9 | 62.0 ( ±4.9) |
| Uncharacterized Proteins (9) | 41.5–70.3 | 64.3 ( ±7.2) |
| All proteins (108) | 44.4–75.3 | 60.8 ( ±5.2) |

[a]Number of genes in class given in parentheses.
[b]Standard deviations given in parentheses.
[c]Combined groups mean ignored in mean calculation.

to be heterologously expressed. The new DNA sequence is designed using codon bias information so that it corresponds to the most preferred codons of the desired plant. The new sequence is then analyzed for restriction enzyme sites that might have been created by the modification. The identified sites are further modified by replacing the codons with second or third choice with preferred codons. Other sites in the sequence which could affect transcription or translation of the gene of interest are the exon:intron 5' or 3' junctions, poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

It is preferred that the plant optimized gene(s) encoding a Xenorhabdus toxin contain about 63% of first choice codons, between about 22% to about 37% second choice codons, and between about 15% to about 0% third choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 2. The method described above enables one skilled in the art to modify gene(s) that are foreign to a particular plant so that the genes are optimally expressed in plants. The method is further illustrated in pending PCT application WO 97/13402, which is incorporated herein by reference.

In order to design plant optimized genes encoding a Xenorhabdus toxin, the amino acid sequence of said protein is reverse translated into a DNA sequence utilizing a non-redundant genetic code established from a codon bias table compiled for the gene sequences for the particular plant, as shown in Table 2. The resulting DNA sequence, which is completely homogeneous in codon usage, is further modified to establish a DNA sequence that, besides having a higher degree of codon diversity, also contains strategically placed restriction enzyme recognition sites, desirable base composition, and a lack of sequences that might interfere with transcription of the gene, or translation of the product mRNA.

In another aspect of the invention, genes encoding the Xenorhabdus toxin are expressed from transcriptional units inserted into the plant genome. Preferably, said transcriptional units are recombinant vectors capable of stable integration into the plant genome and selection of transformed plant lines expressing mRNA encoding for said desaturase proteins are expressed either by constitutive or inducible promoters in the plant cell. Once expressed, the mRNA is translated into proteins, thereby incorporating amino acids of interest into protein. The genes encoding a Xenorhabdus toxin expressed in the plant cells can be under the control of a constitutive promoter, a tissue-specific promoter or an inducible promoter as described herein.

Several techniques exist for introducing foreign recombinant vectors into plant cells, and for obtaining plants that stably maintain and express the introduced gene. Such techniques include acceleration of genetic material coated onto microparticles directly into cells (U.S. Pat. No. 4,945,050 to Cornell and U.S. Pat. No. 5,141,131 to DowElanco, now Dow AgroSciences, LLC). In addition, plants may be transformed using Agrobacterium

TABLE 2

Preferred amino acid codons for proteins expressed in maize.

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Pnenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

*The first and second preferred codons for maize.

technology, see U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to Max Planck, European Patent Applications 604662, 627752 and U.S. Pat. No. 5,591,616 to Japan Tobacco, European Patent Applications 0267159, and 0292435 and U.S. Pat. No. 5,231,019 all to Ciba Geigy, now Novartis, U.S. Pat. Nos. 5,463,174 and 4,762,785 both to Calgene, and U.S. Pat. Nos. 5,004,863 and 5,159,135 both to Agracetus. Other transformation technology includes whiskers technology, see U.S. Pat. Nos. 5,302,523 and 5,464,765 both to Zeneca. Electroporation technology has also been used to transform plants, see WO 87/06614 to Boyce Thompson Institute, U.S. Pat. No. 5,472,869 and 5,384,253 both to Dekalb, WO9209696 and WO9321335 both to Plant Genetic Systems. Furthermore, viral vectors can also be used in produce transgenic plants expressing the protein of interest. For example, monocotyledonous plant can be transformed with a viral vector using the methods described in U.S. Pat. No. 5,569,597 to Mycogen and Ciba-Giegy, now Novartis, as well as U.S. Pat. Nos. 5,589, 367 and 5,316,931, both to Biosource. All of these transformation patents and publications are incorporated herein by reference.

As mentioned previously, the manner in which the DNA construct is introduced into the plant host is not critical to this invention. Any method which provides for efficient transformation may be employed. For example, various methods for plant cell transformation are described herein and include the use of Ti or Ri-plasmids and the like to perform Agrobacterium mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where Agrobacterium is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the Agrobacterium host is not critical to this invention. The Ti or Ri plasmid containing the T-DNA for recombination may be capable or incapable of causing gall formation, and is not critical to said invention so long as the vir genes are present in said host.

In some cases where Agrobacterium is used for transformation, the expression construct being within the T-DNA borders will be inserted into a broad spectrum vector such as pRK2 or derivatives thereof as described in Ditta et al., (PNAS USA (1980) 77:7347–7351 and EPO 0 120 515, which are incorporated herein by reference. Included within the expression construct and the T-DNA will be one or more markers as described herein which allow for selection of transformed Agrobacterium and transformed plant cells. The particular marker employed is not essential to this invention, with the preferred marker depending on the host and construction used.

For transformation of plant cells using Agrobacterium, explants may be combined and incubated with the transformed Agrobacterium for sufficient time to allow transformation thereof. After transformation, the agrobacteria are killed by selection with the appropriate antibiotic and plant cells are cultured with the appropriate selective medium. Once calli are formed, shoot formation can be encourage by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a Xenorhabdus toxin is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue which is contacted with the foreign genes may vary as well. Such tissue would include but would not be limited to embryogenic tissue, callus tissue types I, II, and III, hypocotyl, meristem, root tissue and the like. Almost all plant tissues may be transformed during dedifferentiation using appropriate techniques described herein.

Another variable is the choice of a selectable marker. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialophos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically. not present in the recipient organism or tissue and typically encode for proteins resulting in some phenotypic change or enzymatic property. Examples of such genes are provided in K. Wising et al. Ann. Rev. Genetics, 22, 421 (1988), which is incorporated herein by reference. Preferred reporter genes include the beta-glucuronidase (GUS) of the uida locus of *E. coli,* the chloramphenicol acetyl transferase gene from Tn9 of *E. coli,* the green fluorescent protein from the bioluminescent jellyfish *Aequorea victoria,* and the luciferase genes from firefly *Photinus pyralis.* An assay for detecting reporter gene expression may then be performed at a suitable time after said gene has been introduced into recipient cells. A preferred such assay entails the use of the gene encoding beta-glucuronidase (GUS) of the uida locus of *E. coli* as described by Jefferson et al., (1987 Biochem. Soc. Trans. 15, 17–19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see PCT/US96/1682; WO 97/13402 published Apr. 17, 1997) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression orfunctioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plants' development as well as active in plant tissues and organs. Examples of such include but are not limited to pollen-specific, embryo specific, corn silk specific, cotton fiber specific, root specific, seed endosperm specific promoter regulatory elements and the like. Under certain circumstances it may be desirable to use an inducible promoter regulatory element, which is responsible for expression of genes in response to a specific signal, such as: physical stimulus (heat shock genes); light (RUBP carboxylase); hormone (Em); metabolites; chemical; and stress. Other desirable transcription and translation elements that function in plants may be used. Numerous plant-specific gene transfer vectors are known in the art.

One consideration associated with commercial exploitation of transgenic plants is resistance management. This is of particular concern with *Bacillus thuringiensis* toxins. There are numerous companies commercially exploiting *Bacillus thuringiensis* and there has been much concern about development of resistance to Bt toxins. One strategy for insect resistance management would be to combine the toxins produced by Xenorhabdus with toxins such as Bt, vegetative insecticidal proteins from Bacillus stains (Ciba Geigy; WO 94/21795) or other insect toxins. The combinations could be formulated for a sprayable application or could be molecular combinations. Plants could be transformed with Xenorhabdus genes that produce insect toxins and other insect toxin genes such as Bt.

European Patent Application 0400246A1 describes transformation of a plant with 2 Bts. This could be any 2 genes, not just Bt genes. Another way to produce a transgenic plant that contains more than one insect resistant gene would be to produce two plants, with each plant containing an insect resistance gene. These plants could then be backcrossed using traditional plant breeding techniques to produce a plant containing more than one insect resistance gene.

In addition to producing a transformed plant, there are other delivery systems where it may be desirable to re-engineer the bacterial gene(s). Along the same lines, a genetically engineered, easily isolated protein toxin made by fusing together both a molecule attractive to insects as a food source and the functional activity of the toxin may be engineered and expressed in bacteria or in eukaryotic cells using standard, well-known techniques. After purification in the laboratory such a toxic agent with "built-in" bait could be packaged inside standard insect trap housings.

Another delivery scheme is the incorporation of the genetic material of toxins into a baculovirus vector. Baculoviruses infect particular insect hosts, including those desirably targeted with the Xenorhabdus toxins. Infectious baculovirus harboring an expression construct for the Xenorhabdus toxins could be introduced into areas of insect infestation to thereby intoxicate or poison infected insects.

Insect viruses, or baculoviruses, are known to infect and adversely affect certain insects. The affect of the viruses on insects is slow, and viruses do not immediately stop the feeding of insects. Thus, viruses are not viewed as being optimal as insect pest control agents. However, combining the Xenorhabdus toxin genes into a baculovirus vector could provide an efficient way of transmitting the toxins. In addition, since different baculoviruses are specific to different insects, it may be possible to use a particular toxin to selectively target particularly damaging insect pests. A particularly useful vector for the toxins genes is the nuclear polyhedrosis virus. Transfer vectors using this virus have been described and are now the vectors of choice for transferring foreign genes into insects. The virus-toxin gene recombinant may be constructed in an orally transmissible form. Baculoviruses normally infect insect victims through the mid-gut intestinal mucosa. The toxin gene inserted behind a strong viral coat protein promoter would be expressed and should rapidly kill the infected insect.

In addition to an insect virus or baculovirus or transgenic plant delivery system for the protein toxins of the present invention, the proteins may be encapsulated using *Bacillus thuringiensis* encapsulation technology such as but not limited to U.S. Pat. Nos. 4,695,455; 4,695,462; 4,861,595 which are all incorporated herein by reference. Another delivery system for the protein toxins of the present invention is formulation of the protein into a bait matrix, which could then be used in above and below ground insect bait stations. Examples of such technology include but are not limited to PCT Patent Application WO 93/23998, which is incorporated herein by reference.

Plant RNA viral based systems can also be used to express Xenorhabdus toxin. In so doing, the gene encoding a Xenorhabdus toxin can be inserted into the coat promoter region of a suitable plant virus which will infect the host plant of interest. The Xenorhabdus toxin can then be expressed thus providing protection of the plant from insect damage. Plant RNA viral based systems are described in U.S. Pat. No. 5,500,360 to Mycgoen Plant Sciences, Inc. and U.S. Pat. Nos. 5,316,931 and 5,589,367 to Biosource Genetics Corp. which are incorporated herein by reference.

Standard and molecular biology techniques may be used to clone and sequence the toxins described herein. Additional information may be found in Sambrook, J., Fritsch, E. F., and Maniatis, T. (1989), Molecular Cloning, A Laboratory Manual, Cold Spring Harbor Press, which is incorporated herein by reference.

The following abbreviations are used throughout the Examples: Tris=tris (hydroxymethyl) amino methane; SDS= sodium dodecyl sulfate; EDTA=ethylenediaminetetraacetic acid, IPTG=isopropylthio-B-galactoside, X-gal=5-bromo-4-chloro-3-indoyl-B-D-galactoside, CTAB= cetyltrimethylammonium bromide; kbp=kilobase pairs; dATP, dCTP, dGTP, dTTP, I=2'-deoxynucleoside 5'-triphosphates of adenine, cytosine, guanine, thymine, and inosine, respectively; ATP=adenosine 5' triphosphate.

The particular embodiments of this invention are further exemplified in the Examples. However, those skilled in the art will readily appreciate that the specific experiments detailed are only illustrative of the invention as described more fully in the claims which follow thereafter.

EXAMPLE 1

Characterization of Xenorhabdus Strains

In order to establish that the collection described herein consisted of Xenorhabdus isolates, strains were assessed in terms of recognized microbiological traits that are characteristic of phase I variants of Xenorhabdus and which differentiate it from other Enterobacteriaceae and Photorhabdus spp. [Farmer, J. J. 1984. Bergey's Manual of Systemic Bacteriology, vol 1. pp. 510–511. (ed. Kreig N. R. and Holt, J. G.). Williams & Wilkins, Baltimore.; Akhurst and Boemare, 1988, J. Gen. Microbiol. 134, 1835–1845;

Forst and Nealson, 1996. Microbiol. Rev. 60, 21–43]. These characteristic traits were as follows: Gram stain negative rods; organism size of 0.3–2 μm in width and 2–10 μm in length with occasional filaments (15–50 μm) and spheroplasts; white to yellow/brown colony pigmentation on nutrient agar; presence of crystalline inclusion bodies; absence of catalase; negative for oxidase; inability to reduce nitrate; absence of bioluminescence; ability to take up dye from growth media; positive for protease production; growth-temperature below 37° C.; survival under anaerobic conditions and positively motile (Table 3). Methods were checked using reference *Escherichia coli*, Xenorhabdus and Photorhabdus strains as controls. Overall results shown in Table 3 were consistent with all strains being members of the family Enterobacteriaceae and the genus Xenorhabdus.

A luminometer was used to establish the absence of bioluminescence associated with Xenorhabdus strains. To measure the presence or absence of relative light emitting units, broth from each strain (cells and media) was measured at up to three time intervals after inoculation in liquid culture (24, 48 and/or 72 h) and compared to background luminosity (uninoculated media). Several Photorhabdus strains were also tested as positive controls for luminosity. Prior to measuring light emission from selected broths, cell density was established by measuring $A_{560\ nm}$ in a Gilford Systems (Oberlin, Ohio) spectrophotometer using a sipper cell. The resulting light emitting units were then normalized to cell density. Aliquots of broths were placed into 96-well microtiter plates (100 μL each) and read in a Packard Lumicount luminometer (Packard Instrument Co., Meriden Conn.). The integration period for each sample was 0.1 to 1.0 sec. The samples were agitated in the luminometer for 10 sec prior to taking readings. A positive test was determined as being $\geq$3-fold background luminescence (~1–15 relative light units). In addition, absence of colony luminosity with some strains was confirmed with photographic film overlays and visual analysis after visual adaptation in a darkroom.

The Gram staining characteristics of each strain were established with a commercial Gram-stain kit (BBL, Cockeysville, Md.) in conjunction with Gram stain control slides (Fisher Scientific, Pittsburgh, Pa.). Microscopic evaluation was then performed using a Zeiss microscope (Carl Zeiss, Germany) 100× oil immersion objective lens (with 10× ocular and 2× body magnification). Microscopic examination of individual strains for organism size, cellular description and inclusion bodies (the latter two observations after logarithmic growth) was performed using wet mount slides (10× ocular, 2× body and 40× objective magnification) and phase contrast microscopy with a micrometer (Akhurst, R. J. and Boemare, N. E. 1990. *Entomopathogenic Nematodes in Biological Control* (ed. Gaugler, R. and Kaya, H.). pp. 75–90. CRC Press, Boca Raton, USA.; Baghdiguian S., Boyer-Giglio M. H., Thaler, J. O., Bonnot G., Boemare N. 1993. Biol. Cell 79, 177–185). Colony pigmentation was observed after inoculation on Bacto nutrient agar, (Difco Laboratories, Detroit, Mich.) prepared per label instructions. Incubation occurred at 28° C. and descriptions were recorded after 5–7 days.

To test for the presence of catalase activity, 1 mL of culture broth or a colony of the test organism on a small plug of nutrient agar was placed into a glass test tube. One mL of a household hydrogen peroxide solution was gently added down the side of the tube. A positive reaction was recorded when bubbles of gas (presumably oxygen) appeared immediately or within 5 sec. Negative controls of uninoculated nutrient agar or culture broth and hydrogen peroxide solution were also examined.

The oxidase reaction of each strain was determined by rubbing 24 h colonies onto DrySlide Oxidase slides (Difco, Inc.; Detroit, Mich.). Oxidase positive strains produce a dark purple color, indicative of cytochrome oxidase C, within 20 sec after the organism was rubbed against the slide. Failure to produce a dark purple color indicated that the organism was oxidase negative.

To test for nitrate reduction, each culture was inoculated into 10 mL of Bacto Nitrate Broth (Difco Laboratories, Detroit, Mich.). After 24 h incubation at 28° C., nitrite production was tested by the addition of two drops of sulfanilic acid reagent and two drops of alpha-naphthylamine reagent (Difco Manual, 10th edition, Difco Laboratories, Detroit, Mich., 1984). The generation of a distinct pink or red color indicated the formation of nitrite from nitrate whereas the lack of color formation indicated that the strain was nitrate reduction negative. In the latter case, finely powdered zinc was added to further confirm the presence of unreduced nitrate established by the formation of nitrite and the resultant red color.

The ability of each strain to uptake dye from growth media was tested with Bacto MacConkey agar containing the dye neutral red; Bacto Tergitol-7 agar containing the dye bromothymol blue and Bacto EMB Agar containing the dyes methylene blue and eosin-Y (formulated agars from Difco Laboratories, Detroit, Mich., all prepared according to label instructions). After inoculation on these media, dye uptake was recorded upon incubation at 28° C. for 5 days. Growth on Bacto MacConkey and Bacto Tergitol-7 media is characteristic for members of the family Enterobacteriaceae. Motility of each strain was tested using a solution of Bacto Motility Test Medium (Difco Laboratories, Detroit, Mich.) prepared per label instructions. A butt-stab inoculation was performed with each strain and positive motility was judged after incubation at 28° C. by macroscopic observation of a diffuse zone of growth spreading from the line of inoculation.

The production of protease was tested by observing ihydrolysis of gelatin using Bacto gelatin (Difco Laboratories, Detroit, Mich.) plates made per label instructions. Cultures were inoculated and the plates were incubated at 22° C. for 3–5 days prior to assessment of gelatin hydrolysis. To assess growth at different temperatures, agar plates [2% proteose peptone #3 with two percent Bacto-Agar (Difco, Detroit, Mich.) in deionized water] were streaked from a common source of inoculum. Plates were incubated at 20, 28 and 37° C. for 5 days. The incubator temperatures were checked with an electronic thermocouple and metered to insure valid temperature settings.

Oxygen requirements for Xenorhabdus strains were tested in the following manner. A butt-stab inoculation into fluid thioglycolate broth medium (Difco, Detroit, Mich.) was made. The tubes were incubated at room temperature for one week and cultures were then examined for type and extent of growth. The indicator resazurin was used to indicate the presence of medium oxygenation or the aerobiosis zone (Difco Manual, 10th edition, Difco Laboratories, Detroit, Mich.). In the case of unclear results, the final agar concentration of fluid thioglycolate broth medium was raised to 0.75% and the growth characteristics rechecked.

The diversity of Xenorhabdus strains was measured by analysis of PCR (Polymerase Chain Reaction) mediated genomic fingerprinting using genomic DNA from each strain. This technique is based on families of repetitive DNA sequences present throughout the genome of diverse bacterial species (reviewed by Versalovic, J., Schneider, M., D E Bruijn, F. J. and Lupski, J. R. 1994. Methods Mol. Cell. Biol., 5, 25–40). Three of these, repetitive extragenic palindromic sequence (REP), enterobacterial repetitive intergenic consensus (ERIC) and the BOX element, are thought to play an important role in the organization of the bacterial genome. Genomic organization is believed to be shaped by selection and the differential dispersion of these elements within the genome of closely related bacterial strains can be used to discriminate between strains (e.g. Louws, F. J., Fulbright, D. W., Stephens, C. T. and D E Bruijn, F. J. 1994. Appl. Environ. Micro. 60, 2286–2295). Rep-PCR utilizes oligonucleotide primers complementary to these repetitive sequences to amplify the variably sized DNA fragments lying between them. The resulting products are separated by electrophoresis to establish the DNA "fingerprint" for each strain.

To isolate genomic DNA from strains, cell pellets were resuspended in TE buffer (10 or 50 mM Tris-HCl, 1 or 50 mM EDTA, pH 8.0) to a final volume of 10 mL and 12 mL of 5 M NaCl was then added. This mixture was centrifuged 20 min at 15,000×g. The resulting pellet was resuspended in 5.7 mL of TE and 300 μL of 10% SDS and 60 μL 20 mg/ml proteinase K (Gibco BRL Products, Grand Island, N.Y.) were added. This mixture was incubated at 37° C. for 1 h, about 10 mg of lysozyme was added, and the mixture was then incubated for an additional 30 to 45 min. One mL of 5M NaCl and 800 μL of CTAB/NaCl solution (10% w/v CTAB, 0.7 M NaCl) were then added and the mixture was incubated 10 to 20 min at 65° C., and in some cases, gently agitated, then incubated and agitated for an additional 20 min to aid in clearing of the cellular material. An equal volume of chloroform/isoamyl alcohol solution (24:1, v/v) was added, mixed gently then centrifuged. Two extractions were performed with an equal volume of phenol/chloroform/isoamyl alcohol (PCI; 50:49:1). Genomic DNA was precipitated with 0.6 volume of isopropanol. Precipitated DNA was removed with a sterile plastic loop or glass rod, washed twice with 70% ethanol, dried

TABLE 3

Taxonomic Traits of Xenorhabdus Strains

| Strain | A* | B | C | D | E | F | G | H | I | J§ | K | L | M | N | O | P | Q | R |
|---|---|---|---|---|---|---|---|---|---|---|---|---|---|---|---|---|---|---|
| S. carp | −† | + | − | rd S | + | − | − | + | + | W | + | + | + | + | + | + | − | − |
| X. Wi | − | + | − | rd S | + | − | − | + | + | W | + | + | + | + | + | + | − | − |
| X. nem | − | + | − | rd S | + | − | − | + | + | W | + | + | + | + | + | + | − | − |
| X. NH3 | − | + | − | rd S | + | − | − | + | + | W | + | + | + | + | + | + | − | − |
| X. riobravis | − | + | − | rd S | + | − | − | + | + | W | + | + | + | + | + | + | − | − |
| DEX1 | − | + | − | rd S | + | − | − | + | + | W | + | + | + | + | + | + | − | − |
| DEX6 | − | + | − | rd S | + | − | − | + | + | W | + | + | + | + | + | + | − | − |
| ILM037 | − | + | − | rd S | + | − | − | + | + | C | + | + | + | + | + | + | − | − |
| ILM039 | − | + | − | rd S | + | − | − | + | + | W | + | + | + | + | + | + | − | − |
| ILM070 | − | + | − | rd S | + | − | − | + | + | W | + | + | + | + | + | + | − | − |
| ILM078 | − | + | − | rd S | + | − | − | + | + | W | + | + | + | + | + | + | − | − |
| ILM079 | − | + | − | rd S | + | − | − | + | + | C | + | + | + | + | + | + | − | − |
| ILM080 | − | + | − | rd S | + | − | − | + | + | W | + | + | + | + | + | + | − | − |
| ILM081 | − | + | − | rd S | + | − | − | + | + | W | + | + | + | + | + | + | − | − |
| ILM082 | − | + | − | rd S | + | − | − | + | + | W | + | + | + | + | + | + | − | − |
| ILM083 | − | + | − | rd S | + | − | − | + | + | W | + | + | + | + | + | + | − | − |
| ILM084 | − | + | − | rd S | + | − | − | + | + | W | + | + | + | + | + | + | − | − |
| ILM102 | − | + | − | rd S | + | − | − | + | + | C | + | + | + | + | + | + | − | − |
| ILM103 | − | + | − | rd S | + | − | − | + | + | C | + | + | + | + | + | + | − | − |
| ILM104 | − | + | − | rd S | + | − | − | + | + | C | + | + | + | + | + | + | − | − |
| ILM129 | − | + | − | rd S | + | − | − | + | + | Y | + | + | + | + | + | + | − | − |
| ILM133 | − | + | − | rd S | + | − | − | + | + | Y | + | + | + | + | + | + | − | − |
| ILM135 | − | + | − | rd S | + | − | − | + | + | Y | + | + | + | + | + | + | − | − |
| ILM138 | − | + | − | rd S | + | − | − | + | + | Y | + | + | + | + | + | + | − | − |
| ILM142 | − | + | − | rd S | + | − | − | + | + | Y | + | + | + | + | + | + | − | − |
| ILM143 | − | + | − | rd S | + | − | − | + | + | Y | + | + | + | + | + | + | − | − |
| GLX26 | − | + | − | rd S | + | − | − | + | + | C | + | + | + | + | + | + | − | − |
| GLX40 | − | + | − | rd S | + | − | − | + | + | C | + | + | + | + | + | + | − | − |
| GLX166 | − | + | − | rd S | + | − | − | + | + | C | + | + | + | + | + | + | − | − |
| SEX20 | − | + | − | rd S | + | − | − | + | + | C | + | + | + | + | + | + | − | − |
| SEX76 | − | + | − | rd S | + | − | − | + | + | C | + | + | + | + | + | + | − | − |
| SEX180 | − | + | − | rd S | + | − | − | + | + | C | + | + | + | + | + | + | − | − |
| GL133B | − | + | − | rd S | + | − | − | + | + | Y | + | + | + | + | + | + | − | − |
| DEX2 | − | + | − | rd S | + | − | − | + | + | W | + | + | + | + | + | + | − | − |
| DEX3 | − | + | − | rd S | + | − | − | + | + | Y | + | + | + | + | + | + | − | − |
| DEX4 | − | + | − | rd S | + | − | − | + | + | W | + | + | + | + | + | + | − | − |
| DEX5 | − | + | − | rd S | + | − | − | + | + | W | + | + | + | + | + | + | − | − |
| DEX7 | − | + | − | rd S | + | − | − | + | + | W | + | + | + | + | + | + | ND | − |
| DEX8 | − | + | − | rd S | + | − | − | + | + | W | + | + | + | + | + | + | ND | − |

*: A = Gram's stain, B = Crystaline inclusion bodies, C = Bioluminescence, D = Cell form, E = Motility, F = Nitrate reduction, G = Presence of catalase, H = Gelatin hydrolysis, I = Dye uptake, J = Pigmentation on Nutrient Agar, K = Growth on EMB agar, L = Growth on MacConkey agar, M = Growth on Tergitol-7 agar, N = Facultative anaerobe, O = Growth at 20° C., P = Growth at 28° C., Q = Growth at 37° C., R = oxidase.
†: + = positive for trait, − = negative for trait; rd = rod, S = sized within Genus descriptors, ND = not determined
§: W = white, C = cream, Y = yellow.

and dissolved in 2 mL of STE (10 mM Tris-HCl pH8.0, 10 mM NaCl, 1 mM EDTA). The DNA was then quantitated at $A_{260\ nm}$. In a second method, 0.01 volumes of RNAase A (50 µg/mL final) was added and incubated at 3720 C. for 2 h. The sample was then extracted with an equal volume of PCI. The samples were then precipitated with 2 volumes of 100% ethanol and collected as described above. Samples were then air dried and resuspended in 250–1000 µL of TE.

To perform rep-PCR analysis of Xenorhabdus genomic DNA, the following primers were used: REPLR-I; 5'-IIICGICGICATCIGGC-3' and REP2-I; 5'-ICGICTTATCIGGCCTAC-3'. PCR was performed using the following 25 µL reaction: 7.75 µL $H_2O$, 2.5 µL 10×LA buffer (PanVera Corp., Madison, Wis.), 16 µL dNTP mix (2.5 mM each), 1 µL of each primer at 50 pM/µL, 1 µL DMSO, 1.5 µL genomic DNA (concentrations ranged from 0.075–0.480 µg/µL) and 0.25 µL TaKaRa EX Taq (PanVera Corp., Madison, Wis.). The PCR amplification was performed in a Perkin Elmer DNA Thermal Cycler (Norwalk, Conn.) using the following conditions: 95° C. for 7 min then [94° C. for 1 min, 44° C. for 1 min, 65° C. for 8 min] for 35 cycles; followed by 65° C. for 15 min. After cycling, 25 µL of reaction was added to 5 µL of 6×gel loading buffer (0.25% bromophenol blue, 40% w/v sucrose in $H_2O$). A 15×20 cm 1%-agarose gel was then run in TBE buffer (0.09 M Tris-borate, 0.002 M EDTA) using 8 µL of each reaction. The gel was run for approximately 16 h at 45 V. Gels were then stained in 20 µg/mL ethidium bromide for 1 h and destained in TBE buffer for approximately 3 h. Polaroids photographs of the gels were then taken under UV illumination.

The presence or absence of bands at specific sizes for each strain was scored from the photographs using RFLP scan Plus software (Scanalytics, Billerica, Mass.) and entered as a similarity matrix in the numerical taxonomy software program, NTSYS-pc (Exeter Software, Setauket, N.Y.). Controls of *E. coli* strain HB101 and *Xanthomonas oryzae* pv. *oryzae* assayed under the same conditions produced PCR fingerprints corresponding to published reports (Versalovic, J., Koeuth, T. and Lupski, J. R. 1991. Nucleic Acids Res. 19, 6823–6831; Vera Cruz, C. M., Halda-Alija, L., Louws, F., Skinner, D. Z., George, M. L., Nelson, R. J., D E Bruijn, F. J., Rice, C. and Leach, J. E. 1995. Int. Rice Res. Notes, 20, 23–24.; Vera Cruz, C. M., Ardales, E. Y., Skinner, D. Z., Talag, J., Nelson, R. J., Louws, F. J., Leung, H., Mew, T. W. and Leach, J. E. 1996. Phytopathology 86, 1352–1359). The data from Xenorhabdus strains were then analyzed with a series of programs within NTSYS-pc; SIMQUAL (Similarity for Qualitative data) to generate a matrix of similarity coefficients (using the Jaccard coefficient) and SAHN (Sequential, Agglomerative, Heirarchical and Nested) clustering using the UPGMA method (Unweighted Pair-Group Method with Arithmetic Averages) which groups related strains and can be expressed as a phenogram (FIG. 1). The COPH (cophenetic values) and MXCOMP (matrix comparison) programs were used to generate a cophenetic value matrix and compare the correlation between this and the original matrix upon which the clustering was based. A resulting normalized Mantel statistic (r) was generated which was a measure of the goodness of fit for a cluster analysis (r=0.8–0.9 representing a very good fit). In our case r=0.9, indicated an excellent fit. Therefore, strains disclosed herein were determined to be comprised of a diverse group of easily distinguishable strains representative of the Xenorhabdus genus.

Strains disclosed herein were deposited before application filing with the following International Deposit Authority: Agricultural Research Service Patent Culture Collection (NRRL), National Center for Agricultural Utilization Research, ARS-USDA, 1815 North University St., Peoria, Ill. 61604. The following strains with NRRL designations were deposited Apr. 29, 1997: S. Carp (NRRL-B-21732); X. Wi (NRRL-B-21733); X. nem (NRRL-B-21734); X. NH3 (NRRL-B-21735); *X. riobravis* (NRRL-B-21736); GL 133B (NRRL-B-21737); DEX1 (NRRL-B-21738); DEX2 (NRRL-B-21739); DEX3 (NRRL-B-21740); DEX4 (NRRL-B-21741); DEX 5 (NRRL-B-21742); and DEX 6 (NRRL-B-21743). The remaining strains disclosed herein were deposited with NRRL on Apr. 30, 1998. In all, thirty-nine (39) strains were deposited.

EXAMPLE 2

Functional Utility of Toxin(s) Produced by Various Xenorhabus Strains

"Storage" cultures of the various Xenorhabdus strains were produced by inoculating 175 mL of 2% Proteose Peptone #3 (PP3) (Difco Laboratories, Detroit, Mich.) liquid medium with a phase I variant colony in a 500 mL tribaffled flask with a Delong neck covered with a Kaput closure. After inoculation, flasks were incubated for between 24–72 h at 28° C. on a rotary shaker at 150 rpm. Cultures were then transferred to a sterile bottle containing a sterile magnetic stir bar and then over-layered with sterile mineral oil to limit exposure to air. Storage cultures were kept in the dark at room temperature. These cultures were then used as inoculum sources for the fermentation of each strain. Phase I variant colonies were also stored frozen at −70° C. for use as an inoculum source. Single, phase I colonies were selected from PP3 plates containing bromothymol blue (0.0025%) and placed in 3.0 mL PP3 and grown overnight on a rotary shaker (150 rpm) at 28° C. Glycerol (diluted in PP3) was then added to achieve a final concentration of 20% and the cultures were frozen in aliquots at −70° C. For culture inoculation, a portion of the frozen aliquot was removed aseptically and streaked on PP3 containing bromothymol blue for reselection of phase I colonies.

Pre-production "seed" flasks or cultures were produced by either inoculating 2 mL of an oil over-layered storage culture or by transferring a phase I variant colony into 175 mL sterile medium in a 500 mL tribaffled flask covered with a Kaput closure. Typically, following 16 h incubation at 28° C. on a rotary shaker at 150 rpm, seed cultures were transferred into production flasks. Production flasks were usually inoculated by adding ~1% of the actively growing seed culture to sterile PP3 or tryptic soy broth (TSB, Difco Laboratories, Detroit Mich.). For small-scale productions, flasks were inoculated directly with a phase I variant colony. Production of broths occurred in 500 mL tribaffled flasks covered with a Kaput closure. Production flasks were agitated at 28° C. on a rotary shaker at 150 rpm. Production fermentations were terminated after 24–72 h.

Following appropriate incubation, broths were dispensed into sterile 1.0 L polyethylene bottles, spun at 2600×g for 1 h at 10° C. and decanted from the cell and debris pellet. Broths were then filter sterilized or further broth clarification was achieved with a tangential flow microfiltration device (Pall Filtron, Northborough, Mass.) using a 0.5 µM open-channel poly-ether sulfone (PES) membrane filter. The resulting broths were then concentrated (up to 10-fold) using a 10,000 or 100,000 MW cut-off membrane, M12 ultra-filtration device (Amicon, Beverly Mass.) or centrifugal concentrators (Millipore, Bedford, Mass. and Pall Filtron, Northborough, Mass.) with a 10,000 or 100,000 MW pore size. In the case of centrifugal concentrators, broths were spun at 2000×g for approximately 2 h. The membrane permeate was added to the corresponding retentate to achieve the desired concentration of components greater than the pore size used. Following these procedures, broths were used for biochemical analysis or biological assessment. Heat inactivation of processed broth samples was achieved by heating 1 mL samples at 100° C. in a sand-filled heat block for 10–20 min.

Broth(s) and toxin complex(es) from different Xenorhabdus strains were useful for reducing populations of insects and were used in a method of inhibiting an insect population which comprised applying to a locus of the insect an effective insect inactivating amount of the active described. A demonstration of the breadth of functional activity observed from broths of a selected group of Xenorhabdus strains fermented as described above is shown in Table 4. It is possible that improved or additional functional activities could be detected with these strains through increased concentration of the broth or by employing different fermentation methods as disclosed herein. Consistent with the activity being associated with a protein, the functional activity showed heat lability and/or was present in the high molecular weight retentate (greater than 10 kDa and predominantly greater than 100 kDa) after concentration of the broth.

Culture broth(s) from diverse Xenorhabdus strains showed differential functional activity (mortality and/or growth inhibition) against a number of insects. More specifically, activity was seen against corn rootworm larvae and boll weevil larvae which are members of the insect order Coleoptera. Other members of the Coleoptera include wireworms, pollen beetles, flea beetles, seed beetles and Colorado potato beetle. The broths and purified toxin complex(es) were also active against tobacco budworm, tobacco hornworm, corn earworm and European corn borer which are members of the order Lepidoptera. Other typical members of this order are beet armyworm, cabbage looper, black cutworm, codling moth, clothes moth, Indian mealmoth, leaf rollers, cabbage worm, bagworm, Eastern tent caterpillar, sod webworm and fall armyworm. Activity was also seen against mosquito larvae which are members of the order Diptera. Other members of the order Diptera are, pea midge, carrot fly, cabbage root fly, turnip root fly, onion fly, crane fly and house fly and various mosquito species. Activity with broth(s) was also seen against two-spotted spider mite which is a member of the order Acarina which includes strawberry spider mites, broad mites, citrus red mite, European red mite, pear rust mite and tomato russet mite.

Activity against corn rootworm larvae was tested as follows. Xenorhabdus culture broth(s) (10× concentrated, filter sterilized), PP3 or TSB (10× concentrated), purified toxin complex(es) or 10 mM sodium phosphate buffer, pH 7.0, were applied directly to the surface (about 1.5 cm$^2$) of artificial diet (Rose, R. I. and McCabe, J. M. 1973. J. Econ. Entomol. 66, 398–400) in 40 µL aliquots. Toxin complex was diluted in 10 mM sodium phosphate buffer, pH 7.0. The diet plates were allowed to air-dry in a sterile flow-hood and the wells were infested with single, neonate *Diabrotica undecimpunctata howardi* (Southern corn rootworm, SCR) hatched from surface sterilized eggs. Plates were sealed, placed in a humidified growth chamber and maintained at 27° C. for the appropriate period (3–5 days). Mortality and larval weight determinations were then scored. Generally, 8–16 insects per treatment were used in all studies. Control mortality was generally less than 5%.

Activity against boll weevil (*Anthomonas grandis*) was tested as follows. Concentrated (10×) Xenorhabdus broths or control medium (PP3) were applied in 60 µL aliquots to the surface of 0.35 g of artificial diet (Stoneville Yellow lepidopteran diet) and allowed to dry. A single, 12–24 h boll weevil larva was placed on the diet, the wells were sealed and held at 25° C., 50% relative humidity (RH) for 5 days. Mortality and larval weights were then assessed. Control mortality ranged between 0–25%.

Activity against mosquito larvae was tested as follows. The assay was conducted in a 96-well microtiter plate. Each well contained 200 µL of aqueous solution (10×concentrated Xenorhabdus culture broth(s), control Imedium (2% PP3) and about 20, 1-day old larvae (*Aedes aegypti*). There were 6 wells per treatment. The results were read at 24 h after infestation. No control mortality was observed.

Activity against lepidopteran larvae was tested as follows. Concentrated (10×) Xenorhabdus culture broth(s), control medium (PP3 or TSP), purified toxin complex(es) or 10 mM sodium phosphate buffer, pH 7.0 were applied directly to the surface (~1.5 cm$^2$) of standard artificial lepidopteran diet (Stoneville Yellow diet) in 40 µL aliquots. The diet plates were allowed to air-dry in a sterile flow-hood and each well was infested with a single, neonate larva. European corn borer (*Ostrinia nubilalis*), fall armyworm (*Spodoptera frugiperda*), corn earworm (*Helicoverpa zea*) and tobacco hornworm (*Manduca sexta*) eggs were obtained from commercial sources and hatched in-house whereas tobacco budworm (*Heliothis virescens*) and beet armyworm (*Spodoptera exigua*) larvae were supplied internally. Following infestation with larvae, diet plates were sealed, placed in a humidified growth chamber and maintained in the dark at 27° C. for the appropriate period. Mortality and weight determinations were scored at day 5. Generally, 16 insects per treatment were used in all studies. Control mortality generally ranged from 0–12.5%.

Activity against two-spotted spider mite (*Tetranychus urticae*) was determined as follows. Young squash plants were trimmed to a single cotyledon and sprayed to run-off with 10× concentrated broth(s) or control medium (PP3). After drying, plants were infested with a mixed population of spider mites and held at room temperature and humidity for 72 hr. Live mites were then counted to determine levels of control.

EXAMPLE 3

Functional Activity of Highly Purified Toxin Proteins from Xenorhabdus Strain *X. riobravis*

Functional toxin protein was purified from fermentation broth of Xenorhabdus strain *X. riobravis* as described herein. This toxin was tested against neonate larvae of five insect species, Southern corn rootworm, European cornborer, Tobacco hornworm, Corn earworm and Tobacco budworm following the methods described in Example 2. The results are seen in Table 5. All species showed growth inhibitory and/or lethal effects after five days when presented with toxin at a dose of 440 ng toxin/cm$^2$ diet.

TABLE 4

Observed Functional Spectrum of Broths From Different Xenorhabdus Strains

| Xenorhabdus Strain | Sensitive* Insect Species |
| --- | --- |
| S. carp | 1**, 2, 3, 4, 5, 6, 7 |
| X. riobravis | 1, 2, 3, 5, 6, 7 |

TABLE 4-continued

Observed Functional Spectrum of Broths From Different Xenorhabdus Strains

| Xenorhabdus Strain | Sensitive* Insect Species |
|---|---|
| X. NH3 | 1, 2, 3, 6 |
| X. Wi | 1, 2, 3, 5, 6, 7 |
| X. nem | 3, 5, 6 |
| DEX1 | 1, 2, 3, 6 |
| DEX6 | 1, 2, 3, 4, 5, 6 |
| ILM037 | 1, 4 |
| ILM039 | 4 |
| ILM070 | 4, 8 |
| ILM078 | 3, 4 |
| ILM079 | 3 |
| ILM080 | 3 |
| ILM081 | 3 |
| ILM082 | 3 |
| ILM083 | 3 |
| ILM084 | 3 |
| ILM102 | 1, 2, 4 |
| ILM103 | 1, 3, 4, 8 |
| ILM104 | 3, 4, 8 |
| ILM116 | 1, 4 |
| ILM129 | 1, 4 |
| ILM133 | 1, 4 |
| ILM135 | 1, 2, 4 |
| ILM138 | 4 |
| ILM142 | 1, 2, 3, 4, 8 |
| ILM143 | 4 |
| GLX26 | 8 |
| GLX40 | 3, 8 |
| GLX166 | 4 |
| SEX20 | 1, 4, 8 |
| SEX76 | 1, 4 |
| SEX180 | 4 |
| GL133B | 4 |
| DEX2 | 6, 7 |
| DEX3 | 3, 6 |
| DEX4 | 6, 7 |
| DEX5 | 3, 6 |
| DEX7 | 3 |
| DEX8 | 3 |

* = ≧25% mortality and/or growth inhibition vs. control
** = 1; Tobacco budworm, 2; European corn borer, 3; Tobacco hornworm, 4; Southern corn rootworm, 5; Boll weevil, 6; Mosquito, 7; Two-spotted spider mite, 8; Corn earworm

TABLE 5

Effect of Highly Purified *X. riobravis* Toxin on Various Insect Species

| Treatment | S. corn rootworm | European cornborer | Tobacco hornworm | Corn earworm | Tobacco budworm |
|---|---|---|---|---|---|
| *X. riobravis* | 19/46* | 75/61 | 75/75 | 25/95 | 13/98 |

*Value are the % mortality/% growth inhibition corrected for control effects.

EXAMPLE 4

Effect of Diffferent Culture Media on Functional Activity of Fermentation Broths from Selected Xenorhabdus Strains Several different culture media were used to further optimize conditions for detection of functional activity in the fermentation broths of several Xenorhabdus strains. GL133B, *X. riobravis*, X. Wi, DEX8 and DEX1 were grown in PP3, TSB and PP3 plus 1.25% NaCl (PP3S) as described herein. Broths were then prepared as described herein and assayed against neonate Tobacco hornworm to determine any changes in insecticidal activity. In both experimental cases (condition A which is PP3 vs. TSB; and condition B which is PP3 vs. PP3S), the functional activity of fermentations in PP3S and/or TSB were improved as compared to simultaneous PP3 fermentations (Table 6). In certain cases, activity was uncovered which was not apparent with PP3 fermentations. The functional activity produced under condition A and condition B was shown to be heat labile and retained by high molecular weight membranes (>100,00 kDa). Addition of NaCl to broth after bacterial growth was complete did not increase toxin activity indicating that the increased functional activity observed was not due to increase NaCl concentration in the media but instead due to increased toxin.

The increased activity observed with *X. riobravis* fermented in PP3S was further investigated by partial purification of toxin(s) from fermentations in PP3 and PP3S as described herein. Consistent with observations using culture broth, the active fraction(s) from PP3S broth (obtained from anion exchange and size-exclusion chromatography as described herein) contained increased biological activity, protein concentration and a more complex protein pattern as determined by SDS-PAGE analysis.

TABLE 6

The Effect of Different Culture Media on Functional Potency of Selected Xenorhabdus Fermentation Broths

| | Condition A | | Condition B | |
|---|---|---|---|---|
| Strains | PP3 | TSB | PP3 | PP3S |
| GL133B | −* | − | − | + |
| X. riobravis | + | +++ | + | +++ |
| X. Wi | + | +++ | + | +++ |
| DEX8 | − | + | − | − |
| DEX6 | + | ++ | + | +++ |
| Control | − | − | − | − |

* +=25–50% mortality, ++=51–75% mortality, +++=>76% mortality, −=<25% mortality

EXAMPLE 5

Xenorhiddus Strains X. nem, *X. riobravis*, and X. Wi: Purification, Characterization and Activity The protocol, as follows, was established based on purifying those fractions having the most activity against Tobacco Hornworm (*Manduca sexta*), hereinafter THW, as determined in bioassays (see Example 2). Typically, 4–20 L of Xenorhabdus culture that had been grown in PP3 broth being filtered, as described herein, were received and concentrated using an Amicon spiral ultra filtration cartridge Type S1Y100 attached to an Amicon M-12 filtration device (Amicon Inc., Beverly, Mass.). The retentate contained native proteins wherein the majority consisted of those having molecular sizes greater than 100 kDa, whereas the flow through material contained native proteins less than 100 kDa in size. The majority of the activity against THW was contained in the 100 kDa retentate. The retentate was then continually diafiltered with 10 mM sodium phosphate (pH=7.0) until the filtrate reached an $A_{280}$<0.100. Unless otherwise stated, all procedures from this point were performed in buffer defined as 10 mM sodium phosphate (pH 7.0). The retentate was then concentrated to a final volume of about 0.20 L and then filtered using a 0.45 μm sterile filtration unit (Corning, Corning, N.Y.).

The filtered material was loaded at 7.5 mL/min onto a Pharmacia HR16/10 column which had been packed with PerSeptive Biosystem POROS 50 HQ strong anion exchange matrix equilibrated in buffer using a PerSeptive Biosystem SPRINT HPLC system (PerSeptive Biosystems, Framingham, Mass.). After loading, the column was washed with buffer until an $A_{280\ nm}$<0.100 was achieved. Proteins were then eluted from the column at 2.5 mL/min using buffer with 0.4 M NaCl for 20 min for a total volume of 50 mL. The column was then washed using buffer with 1.0 M NaCl at the same flow rate for an additional 20 min (final volume=50 ml). Proteins eluted with 0.4 M and 1.0 M NaCl were placed in separate dialysis bags (SPECTRA/POR Membrane MWCO: 2,000; Spectrum, Houston, Tex.) and allowed to dialyze overnight at 4° C. in 12 L buffer. In some cases, the 0.4 M fraction was not dialyzed but instead was immediately desalted by gel filtration (see below). The majority of activity against THW was contained in the 0.4 M fraction.

The 0.4 M fraction was further purified by application of 20 mL to a Pharmacia XK 26/100 column that had been prepacked with Sepharose CL4B (Pharmacia) using a flow rate of 0.75 mL/min. Fractionation of the 0.4 M fraction on the Sepharose CL4B column yielded four to five distinct peaks when purifying X. nem and X. Wi. Proteins from strain *X. riobravis,* while having a distinct peak equivalent to the void volume, also had a very broad, low absorbance region ranging from ca. 280 min to ca. 448 min of the 800 min run. Typically, two larger absorbance peaks were observed after 450 min and before 800 min. Active fractions from X. Wi and X. nem typically eluted at about 256 min to 416 min of a 800 min run.

Fractions were pooled based on $A_{280\ nm}$ peak profile and concentrated to a final volume of 0.75 ml using a Millipore ULTRAFREE-15 centrifugal filter device Biomax-50K NMWL membrane (Millipore Inc., Bedford, Mass.) or concentrated by binding to a Pharmacia MonoQ HR10/10 column, as described herein. Protein concentrations were determined using a BioRad Protein Assay Kit (BioRad, Hercules, Calif.) with bovine gamma globulin as a standard.

The native molecular weight of the THW toxin complex was determined using a Pharmacia HR 16/50 column that had been prepacked with Sepharose CL4B in said phosphate buffer. The column was then calibrated using proteins of known molecular size thereby allowing for calculation of the toxin complex approximate native molecular size. As shown in Table 7, the molecular size of the toxin complex were as follows: 1500±530 kDa for strain X. nem; 1000±350 kDa for strain *X. riobravis;* 3290 kDa+1150 kDa for strain X. Wi; 980±245 for strain ILM078; 1013±185 for strain DEX6; and 956±307 for strain ILM080. A highly purified fraction of X. Wi, said fraction being purified via ion exchange, gel filtration, ion exchange, hydrophobic interaction chromatography, and ion exchange chromatography as disclosed herein was then analyzed for size using quantitative gel filtration. This material was found to have a native molecular size of 1049±402 kDa (Table 7).

Proteins found in the toxin complex were examined for individual polypeptide size using SDS-PAGE analysis. Typically, 20 μg protein of the toxin complex from each strain was loaded onto a 2–15% polyacrylamide gel (Integrated Separation Systems, Natick, Mass.) and electrophoresed at 20 mA in SDS-PAGE buffer (BioRad). After completion of electrophoresis, the gels were stained overnight in BioRad Coomassie blue R-250 (0.2% in methanol: acetic acid: water; 40:10:40 v/v/v). Subsequently, gels were destained in methanol:acetic acid: water; 40:10:40 (v/v/v). Gels were then rinsed with water for 15 min and scanned using a Molecular Dynamics PERSONAL LASER DENSITOMETER (Sunnyvale, Calif.). Lanes were quantitated and molecular sizes were calculated as compared to BioRad high molecular weight standards, which ranged from 200–45 kDa.

Sizes of individual polypeptides comprising the THW toxin complex from each strain are listed in Table 8. The sizes of the individual polypeptides ranged from 32 kDa to 330 kDa. Each of X. Wi, X. nem, *X. riobravis,* ILM080, ILM078, and DEX6 strains had polypeptides comprising the toxin complex that were in the 160–330 kDa range, the 100–160 kDa range, and the 50–80 kDa range. These data indicate that the toxin complex may vary in peptide composition and components from strain to strain; however, in all cases the toxin attributes appears to consist of a large, oligomeric protein complex with subunits ranging from 23 kDa to 330 kDa.

EXAMPLE 5

Sub-Fraction of Xenorhabdus Toxin Complex from X. riobravis amd X. Wi

For subfractionation, about 10 mg of the Xenorhabdus protein toxin complex of *X. riobravis* was isolated as described above and was applied to a Pharmacia MonoQ HR 10/10 column equilibrated with 10 mM phosphate buffer, pH 7.0 at a flow rate of 2 mL/min. The column was washed with said buffer until the absorbance at 280 nm returned to baseline. Proteins bound to the column were eluted with a linear gradient of 0 to 1.0 M NaCl in said buffer at 2 mL/min for 1 h. Two mL fractions were collected and subjected to analysis by bioassay against THW as described herein. Peaks of activity were determined by examining a 2-fold dilution of each fraction in THW bioassays. A peak of activity against THW was observed that eluted at about 0.3–0.4 M NaCl. The fractions having activity against THW were pooled and analyzed by SDS-PAGE gel electrophoresis. It was observed that there were four predominant peptides having the approximate sizes of 220 kDa, 190 kDa, 130 kDa, and 54 kDa.

The peptides described above were electrophoresed on a 4–20% SDS-PAGE (Integrated Separation Systems) and transblotted to PROBLOTT PVDF membranes (Applied Biosystems, Foster City, Calif.). Blots were sent for amino acid analysis and N-terminal amino acid sequencing at Harvard MicroChem and Cambridge ProChem, respectively. The amino terminal sequence of the 220 kDa protein is entered herein as SEQ ID NO:4.

For sub-fractionation experiments with X. Wi, ca. 10 mg toxin was applied to a MonoQ HR 10/10 column equilibrated with 10 mM phosphate buffer, pH 7.0 at a flow rate of 2 mL/min. The column was washed with said buffer until the $A_{280\ nm}$ returned to baseline. Proteins bound to the column were eluted with a linear gradient of 0 to 1.0 M NaCl in said buffer at 2 mL/min for 1 h. Two mL fractions were collected and subjected to analysis by bioassay against THW as described herein. At least two major detectable peaks at $A_{280\ nm}$ were observed. The majority of functional THW activity that was observed eluted at about 0.10–0.25 M NaCl. The fractions having activity against THW were pooled and analyzed by gel electrophoresis. By SDS-PAGE it was observed that there were up to eight predominant peptides having the approximate sizes of 330 kDa, 320 kDa, 270 ka, 220 kDa, 200 kDa, 190 kDa, 170 kDa, 130 kDa, 91 kDa, 76 kDa, 55 kDa and 36 kDa.

The peak THW pooled activity fraction was applied to phenyl-sepharose HR 5/5 column. Solid $(NH_4)_2SO_4$ added to a final concentration of 1.7 M. The solution was then applied onto the column equilibrated with 1.7 M $(NH_4)_2SO_4$ in 50 mM potassium phosphate buffer, pH 7, at 1 mL/min. Proteins bound to the column were then eluted with a linear gradient of 1.7 M $(NH_4)_2SO_4$, 50 mM potassium phosphate, pH 7.0 to 10 mM potassium phosphate, pH 7.0 at 0.5 mL/min for 60 min. After THW bioassays, it was determined that the peak activity eluted at an $A_{280\ nm}$ between 40 mm to Ca. 50 min. Fractions were dialyzed overnight against 10 mM sodium phosphate buffer, pH 7.0. By SDS-PAGE it was observed that there were up to six predominant peptides having the approximate sizes of 270 kDa, 220 kDa, 170 kDa, 130 kDa, and 76 kDa.

The peptides from THW active fractions from either 5/5 or 10/10 phenyl-sepharose column were electrophoresed on a 4–20% SDS-PAGE gel (Integrated Separation Systems) and transblotted to PROBLOTT PVDF membranes (Applied Biosystems, Foster City, Calif.). Blots were sent for amino acid analysis and N-terminal amino acid sequencing at Harvard MicroChem and Cambridge ProChem, respectively. The N-terminal amino acid sequences for 130 kDa (SEQ ID NO:1), 76 kDa (SEQ ID NO:2), 48 kDa (SEQ ID NO:5) and 38 kDa (SEQ ID NO:3) peptides are entered herein.

Insect bioassays were performed using either toxin complex or THW phenyl-sepharose purified fractions. Functional activity (at least 20% mortality) and/or growth inhibition (at least 40%) was observed for fall armyworm, beet armyworm, tobacco hornworm, tobacco budworm, European corn borer, and southern corn rootworm. In toxin complex preparations tested, higher activity was observed against tobacco hornworm and tobacco budworm than against southern corn rootworm larvae. The insect activity of X. Wi toxin complex and any additionally purified fractions were shown to be heat sensitive.

TABLE 7

Characterization of a Toxin Complex From Xenorhabdus Strains

| STRAIN | TOXIN COMPLEX SIZE[a] |
| --- | --- |
| X. Wi | 3290 kDa ± 1150 kDa |
| X. Wi (Highly Purified) | 1049 kDa ± 402 kDa |
| X. nem | 1010 kDa ± 350 kDa |
| X. riobravis | 1520 kDa ± 530 kDa |
| ILM 078 | 980 kDa ± 245 kDa |
| ILM 080 | 1013 kDa ± 185 kDa |
| DEX6 | 956 kDa ± 307 kDa |

[a]Native molecular weight determined using a Pharmacia HR16/50 column packed with Sepharose CL4B. Highly purified X. Wi was from a fraction isolated from a Mono Q 5/5 column.

TABLE 8

Molecular Sizes of Peptides in Toxin Complex from Xenorhabdus Strains in kDa.

| X. Wi | X. nem | X. riobravis | ILM 080 | ILM 078 | DEX 6 |
| --- | --- | --- | --- | --- | --- |
| 330 | 220 | 220 | 200 | 203 | 201 |
| 320 | 190 | 190 | 197 | 200 | 181 |
| 270 | 170 | 100 | 173 | 173 | 148 |
| 220 | 150 | 96 | 112 | 150 | 138 |
| 200 | 140 | 92 | 106 | 144 | 128 |
| 190 | 85 | 85 | 90 | 106 | 119 |
| 170 | 79 | 79 | 80 | 80 | 90 |
| 130 | 65 | 65 | 74 | 62 | 75 |
| 91 | 56 | 56 | 61 | 58 | 65 |
| 76 | 50 | 50 | 60 | 54 | 59 |
| 55 | 42 | 47 | 58 | 50 | 55 |
| 49 | 38 | 42 | 55 | 45 | 45 |
| 46 | 31 | 38 | 53 | | 41 |
| 43 | 29 | 34 | 48 | | 37 |
| 40 | 26 | 31 | 46 | | 32 |
| 36 | | 26 | 43 | | |
| 32 | | 23 | 42 | | |
| | | | 40 | | |

EXAMPLE 6

Production, Isolation, and Characterization of Xenorhabdus Strain X. carpocapsae A 1% inoculum of an overnight culture of the isolate X. carpocapsae, also known as X. carp, was added to a 125 mL flask containing 25 mL PP3 and incubated for 72 h at 28° C. on a rotary shaker at 250 rpm. Afterwards, the cultures were centrifuged for 20 min at 10,000×g as described herein followed by filtration of the supernatant using a 0.2 μm membrane filter. A 15 mL sample of the supernatant was then added to an Ultrafree-15 100,000 NMWL centrifugal filter device (Millipore, Mass.) and centrifuged at 2000×g. The retentate was washed 2× with 100 mM $KPO_4$, pH 6.9, and then resuspended in 1.0 mL of the same. Proteins were analyzed by SDS-PAGE as disclosed herein using a 10% resolving gel and 4% stacking gel with sizes calibrated using BioRad prestained standards (Hercules, Calif.). Gels were electrophoresed at 40V for 16 h at 15° C. and then stained with Colloidal Blue from Novex, Inc., (San Diego, Calif.).

For additional separations, samples were applied to a BIO-SEP S4000 column (Phenomenex, Torrance, Calif.), 7.5 mm I.D., 60 cm CML under an isocratic system using 100 mM $KPO_4$ pH 6.9. Total amount loaded per sample was 250–500 μg protein. Fractions were collected in 3 groups depending on protein size (size exclusion chromatography) as follows: proteins greater than 1,000 kDa; proteins being 800–1,000 kDa; and proteins less than 800,000 kDa. The 800,000–1,000,000 Da fraction was selected for further analysis.

The 800–1000 kDa fractions, which had the most functional activity, were pooled and concentrated using a 100,000 NMWL centrifugal filter devices (Millipore, Bedford, Mass.). Each pooled retentate fraction was washed 2× and resuspended in 300 μL of 100 mM $KPO_4$ pH 6.9. The protein concentrations were determined using the bicinchoninic acid protein assay reagent kit (Pierce, Rockford, Ill.). Proteins in this fraction were analyzed by SDS-PAGE as described herein and found to have many proteins of different sizes. This material was then further separated on a DEAE column whereby proteins were eluted with increasing salt concentrations. Those fractions having the most activity were then examined again via SDS-PAGE and were found to be comprised of 4 predominate proteins having sizes as follows: 200, 190, 175 and 45 kDa. The active fraction from the DEAE step was passed through a HPLC gel filtration column as described above (BioSep S4000) and the toxic activity against Manduca sexta was found to be contained within a fraction having native proteins >800 kDa. Resolution of this fraction via SDS-PAGE revealed only one protein, said protein having a denatured size of 200 kDa. These data suggest that the 200 kDa protein is responsible for the *Manduca sexta* functional activity (see below) and is possibly found as a tetramer in the culture broth.

Bioassays were performed as follows. Eggs of *M. sexta* were purchased from Carolina Biological Supply Co. The eggs were hatched and reared on fresh wheat germ diet (ICN, CA) while incubated at 25° C. in a 16 h light/8 h dark photocycle incubator. Oral toxicity data were determined by placing twelve *M. sexta* larva onto a piece of insect food containing 300 µg ultrafiltration retentate obtained as described above. Observations were made over 5 days. For the HPLC-size exclusion chromatography fractions, 20 µg total protein were applied to wheat germ diet. Experiment was repeated in duplicate.

We claim:
1. A biologically pure microorganism culture comprising a Xenorhabdus strain selected from the group consisting of

| | |
|---|---|
| S. carp | NRRL-B-21732, |
| X. Wi | NRRL-B-21733, |
| X. nem | NRRL-B-21734, |
| X. NH3 | NRRL-B-21735, |
| X. riobravis | NRRL-B-21736 |
| GL133B | NRRL-B-21737, |
| ILM037 | NRRL-B-30009, |
| ILM039 | NRRL-B-30010, |
| ILM070 | NRRL-B-30011, |
| ILM078 | NRRL-B-30012, |
| ILM079 | NRRL-B-30013, |
| ILM080 | NRRL-B-30014, |
| ILM081 | NRRL-B-30015, |
| ILM082 | NRRL-B-30016, |
| ILM083 | NRRL-B-30017, |
| ILM084 | NRRL-B-30018, |
| ILM102 | NRRL-B-30019, |
| ILM103 | NRRL-B-30020, |
| ILM104 | NRRL-B-30021, |
| ILM129 | NRRL-B-30022, |
| ILM133 | NRRL-B-30023, |
| ILM135 | NRRL-B-30024, |
| ILM138 | NRRL-B-30025, |
| ILM142 | NRRL-B-30026, |
| ILM143 | NRRL-B-30027, |
| GLX26 | NRRL-B-30002, |
| GLX40 | NRRL-B-30003, |
| GLX166 | NRRL-B-30004, |
| SEX20 | NRRL-B-30005, |
| SEX76 | NRRL-B-30006, and |
| SEX180 | NRRL-B-30007. |

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: Xenorhabdus Wi

<400> SEQUENCE: 1

Asn Gln Asn Val Glu Pro Ser Ala Gly Asp Ile Val
  1               5                  10

<210> SEQ ID NO 2
<211> LENGTH: 8
<212> TYPE: PRT
<213> ORGANISM: Xenorhabdus Wi

<400> SEQUENCE: 2

Ser Gln Asn Val Tyr Arg Tyr Pro
  1               5

<210> SEQ ID NO 3
<211> LENGTH: 7
<212> TYPE: PRT
<213> ORGANISM: Xenorhabdus Wi

<400> SEQUENCE: 3

Met Thr Lys Gln Glu Tyr Leu
  1               5

<210> SEQ ID NO 4
<211> LENGTH: 11
<212> TYPE: PRT
<213> ORGANISM: Xenorhabdus Wi

<400> SEQUENCE: 4

Met Tyr Ser Thr Ala Val Leu Leu Asn Lys Ile
  1               5                  10

<210> SEQ ID NO 5
<211> LENGTH: 12
<212> TYPE: PRT
<213> ORGANISM: Xenorhabdus Wi
<220> FEATURE:
<221> NAME/KEY: UNSURE
<222> LOCATION: (11)

<400> SEQUENCE: 5

Ala Gly Phe Gln Leu Asn Glu Tyr Ser Thr Xaa Gly
  1               5                  10
```